United States Patent [19]

Sugimoto

[11] Patent Number: 5,174,155
[45] Date of Patent: Dec. 29, 1992

[54] ULTRASONIC PIPE INSPECTION SYSTEM

[75] Inventor: Sachirou Sugimoto, Kanagawa, Japan

[73] Assignee: Mitsubishi Denki Kabushiki Kaisha, Japan

[21] Appl. No.: 665,265

[22] Filed: Mar. 6, 1991

[30] Foreign Application Priority Data

Mar. 7, 1990 [JP] Japan ................. 2-22779[U]

[51] Int. Cl.⁵ .................. G01N 29/10; G01N 29/26
[52] U.S. Cl. ...................................... 73/622; 73/625; 73/628; 73/644
[58] Field of Search .............. 73/592, 596, 618, 619, 73/620, 622, 625, 627, 628, 640, 644, 637, 638, 633, 641

[56] References Cited

U.S. PATENT DOCUMENTS

| | | | |
|---|---|---|---|
| 3,501,947 | 3/1970 | Hetherington | 73/640 |
| 3,533,281 | 10/1970 | Hetherington | 73/640 |
| 3,672,211 | 6/1972 | Hatch | 73/633 |
| 4,554,835 | 11/1985 | Sakuragi et al. | 73/640 |
| 5,007,291 | 4/1991 | Walters et al. | 73/640 |

Primary Examiner—Hezron E. Williams
Assistant Examiner—Rose M. Finley
Attorney, Agent, or Firm—Wolf, Greenfield & Sacks

[57] ABSTRACT

An ultrasonic search system comprises a hollow nozzle block including a plurality of radial nozzle openings, and a probe holder disposed in coaxial relation to the nozzle block and cooperating with the nozzle block to define an annular passage therebetween. A plurality of probes are mounted within the probe holder in radial alignment with the nozzle openings and extend radially from the inner surface of the probe holder toward the nozzle openings, respectively. Water is supplied to the annular passage and injected from the nozzle openings to a test piece of a circular section such as a steel pipe. The test piece passes through the hollow nozzle block while the nozzle block and the probe holder are rotated by an electric motor. Ultrasonic waves are transmitted from the probes through the nozzle openings into the test piece so as to detect flaws in the test piece by reflections.

8 Claims, 2 Drawing Sheets

ULTRASONIC PIPE INSPECTION SYSTEM

BACKGROUND OF THE INVENTION

1. Field of the Invention

The present invention relates generally to ultrasonic metal inspection and more particularly, to an ultrasonic search system of the type in which a plurality of ultrasonic sensors or probes transmit ultrasonic waves into a test piece of a circular section to determine the presence of flaws by reflections while a probe holder is being rotated about the axis of the test piece.

2. Description of the Related Art

Various ultrasonic search or metal inspection systems have been proposed to scan a test piece such as a steel pipe or a round rod so as to detect flaws in the test piece. An exemplary prior art ultrasonic search system is disclosed in Japanese Laid-Open Utility Model Application No. 66863/81 and includes an inner sleeve or nozzle block through which a test piece passes. An outer sleeve or probe holder is disposed in coaxial relation to the nozzle block so as to define an annular space or passage therebetween. The nozzle block and the probe holder are both driven for rotation around the test piece. A plurality of ultrasonic sensors, commonly referred to as a probe, extend radially through the probe holder and into the passage. The nozzle block has a plurality of nozzle openings in radial alignment with the probes. While the probe holder and the probes are rotated at a high speed, water under pressure is introduced into the annular passage and then, injected from the nozzle openings toward the test piece to form a water column. Ultrasonic waves are transmitted from the probes through the water column into the test piece. Now that the probes are rotated about the axis of the elongate test piece, the test piece can be scanned in a spiral fashion. This metal inspection method enables rapid and accurate scanning or inspection of a test piece of a circular section.

When the probe holder is rotated at a high speed, for example 1,000 r.p.m., the resulting centrifugal force causes water to leak from a portion of the probe holder to which the probes are secured. It will be appreciated that a water column must be maintained between each probe and a test piece to provide an acoustic coupling therebetween. To prevent water leakage, attempts have been made to more firmly secure the probes to the probe holders with a larger number of screws or similar means. However, this results in an increase in the time required to replace the existing probes. Such replacement is required when a new test piece of a different diameter is to be inspected.

SUMMARY OF THE INVENTION

Accordingly, it is an object of the present invention to provide an ultrasonic search system which provides an improved seal between a probe holder and probes, and which enables easy removal for replacement of probes.

According to one embodiment of the present invention, there is provided an ultrasonic search or metal inspection system which includes a hollow nozzle block having a plurality of radial nozzle openings, and a probe holder coaxially disposed in spaced relation to the nozzle block. The nozzle block and the probe holder cooperate together to define an annular passage therebetween. An electric motor is connected to rotate the nozzle block and the probe holder about their own axes. A couplant or water source is communicated with the annular passage. Water under pressure is supplied from the water source to the annular passage and injected from the nozzle openings to an elongate test piece. The test piece has a substantially circular section and is, typically, a steel pipe. The test pipe passes through the hollow nozzle block along a straight line while the nozzle block and the probe holder together with the probes are rotated about the axis of the test piece. A plurality of ultrasonic sensors or probes are mounted to transmit ultrasonic waves through the nozzle openings into the test piece to detect flaws in the test piece by reflections.

According to the present invention, the probes extend radially from the inner surface of the probe holder toward the respective nozzle openings. Each probe is attached to a probe casing to form a probe unit. Preferably, the inner surface of the probe holder is recessed to receive the probe casing. The recess and the probe casing preferably have flat bottoms. When the probe is rotated about its own axis, a centrifugal force is exerted on the probe unit so as to press the probe unit against the inner surface of the probe holder or the flat bottom of the recess. This enhances the integrity of a seal between the probe unit and the probe holder and thus, minimizes water leakage. Under the circumstances, a water column can safely be formed between the probes and the test piece with a lesser amount of water. A further advantage of this system is that since the probes are pressed against the inner wall of the probe holder during rotation of the probe holder, the probes can be firmly held in place only by a single screw. This enables easy removal for replacement of the existing probes.

BRIEF DESCRIPTION OF THE DRAWINGS

A better understanding of the present invention may be had by reference to the following description of a preferred embodiment when taken in conjunction with the accompanying drawings, in which.

DESCRIPTION OF THE PREFERRED EMBODIMENT

Figure 1:
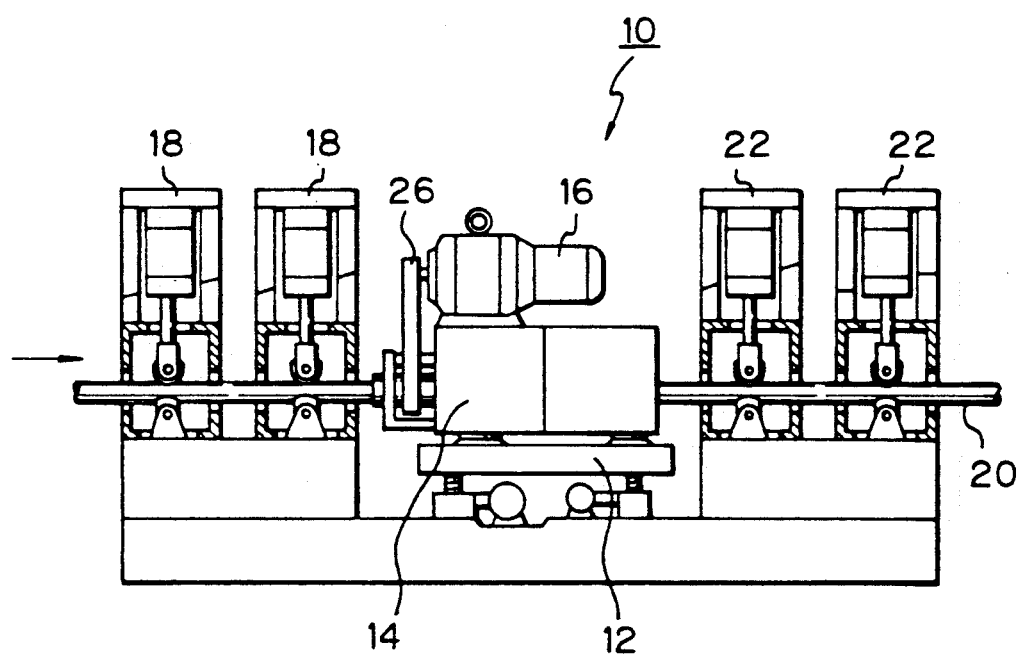
FIG. 1 is a schematic view of an ultrasonic search system according to one embodiment of the present invention.

With now reference to FIG. 1, there is illustrated an ultrasonic search or metal inspection system made according to one embodiment of the present invention and generally indicated by the reference numeral 10. The ultrasonic search system 10 generally includes a vertically movable base 12, a metal inspection body 14 placed on the base 12, and a drive source 16, such as an electric motor, mounted on the inspection body 14. A plurality of sets of pinch rolls 18 are arranged upstream of the body 14 to feed a test piece 20 to the inspection body 14. Also, a plurality of sets of pinch rolls 22 are arranged downstream of the body 14 to receive the test piece 20. The pinch rolls 18 and 22 are designed to restrain vibrations of the test piece 20. The test piece 20 has a substantially circular section and is typically an elongate steel pipe fed from a production line (not shown).

Figure 2:
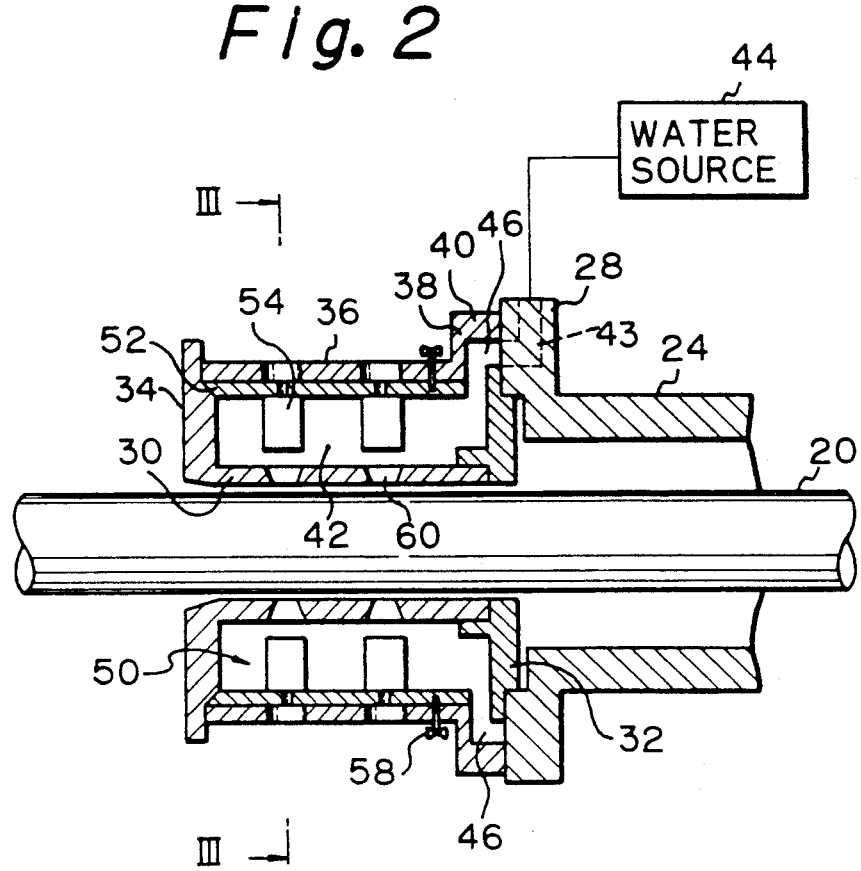
FIG. 2 is a longitudinal sectional view, on an enlarged scale, showing the principal part of the ultrasonic search system shown in FIG. 1.
Figure 3:
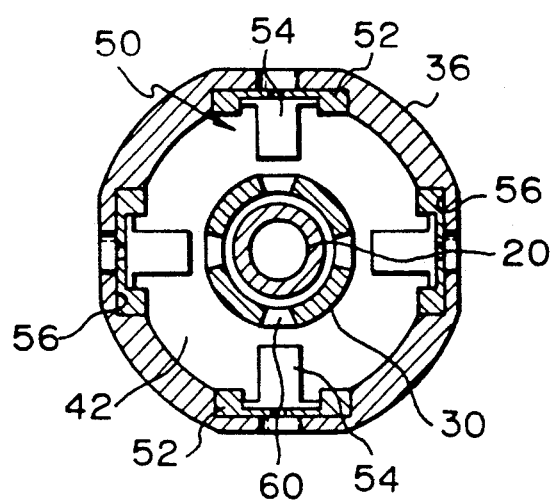
FIG. 3 is a transverse sectional view, on an enlarged scale, taken along the line III—III of FIG. 2.

With reference to FIGS. 2 and 3, the inspection body 14 includes a support or mount 24 connected to the electric motor 16 through a timing belt 26. The mount 24 is driven for rotation about the axis of the test piece 20 and has an integral flange 28. An inner sleeve or nozzle block 30 has one end coupled to the flange 28 of the mount 24 through a ring 32. A flange 34 extends radially outwardly from the other end of the nozzle block 30. An outer sleeve or probe holder 36 is disposed in coaxial relation to the nozzle block 30 and has one end coupled to the flange 34 of the nozzle block 30. A flange 38 extends radially outwardly from the other end of the probe holder 36. An annular projection 40 extends from the outer periphery of the flange 38 of the probe holder 36 to join the flange 28 of the mount 24. An annular passage 42 is defined between the nozzle block 30 and the probe holder 36. Water as a couplant is fed from a water source 44 to the annular space or passage 42 through an inlet port 46 which is defined by the annular projection 40 and the ring 32. The nozzle block 30 is sized to define a predetermined clearance between the inner surface of the nozzle block 30 and the outer surface of the test piece 20.

As better shown in FIG. 3, a plurality of ultrasonic sensors or probe units 50 are mounted to the inner surface of the probe holder 36 in a circumferentially equally spaced relationship. Each probe unit 50 generally includes a casing 52 and probes 54 attached to the casing 52 and extending radially from the inner surface of the probe holder 36 toward the test piece 20. The inner surface of the probe holder 36 is recessed as at 56 to receive the probe casings 52. The probe casings 52 are secured in place by respective screws 58 (see FIG. 2). It is preferred that the probe casing 52 and the recess 56 have flat bottoms. The nozzle block 30 has a plurality of radial nozzle openings or outlet ports 60 in radial alignment with the probes 54.

In use, the test piece 20 is fed into the inspection body 14 by the pinch rolls 22 while travelling along a straight line. The test piece 20 then enters into the nozzle block 30. At this time, the nozzle block 30 and the probe holder 36 have already been rotated by the electric motor 16 at a speed, for example, of 1,000 r.p.m. Water under pressure is supplied from the water source 44 into the passage 43 through the inlet port 46 and then, injected from the nozzle opening or outlet ports 60 to form a water column between each probe and the test piece. The probes 54 are rendered operative to transmit ultrasonic waves into the test piece 20 through the water column so as to determine the presence of flaws by reflections. While the test piece 20 is being fed through the inspection housing 14, it is scanned in a spiral fashion.

When the probe holder 36 is rotated at a high speed, the probe units 50 are subject to a centrifugal force. As a result, the probe units 50 are pressed against the bottom of the respective recesses 56 of the probe holder 36 to provide an effective seal between the probe units 50 and the probe holder 36. It will be understood that the greater the speed of rotation of the electric motor 16 or the probe holder 36, the greater the centrifugal force applied to the probe units 50. The probe units are pressed against the inner surface of the probe holder 36 under the influence of a centrifugal force when the probe holder is rotated. This minimizes the number of screws necessary to secure each probe unit to the probe holder 36 and thus, enables easy removal for replacement of the existing probe units.

When another test piece of a diameter larger than that of the existing test piece 20 is to be inspected, the nozzle block 30 is disconnected from the mount 24 and the probe holder 36 and then, replaced with another nozzle block of a larger diameter to ensure a predetermined clearance between the new test piece and nozzle block. This also necessitates replacement of the existing probe units. The screw 58 is rotated to disconnect each probe unit from the probe holder 36. The probe unit 50 is then slid in a direction away from the mount 24. Another probe unit of a different size is, thereafter, inserted into the probe holder 36 so that a probe casing may be fitted in the recess of the probe holder 36. The screw 58 is again used to secure the new probe unit to the probe holder 36. In the illustrated embodiment, a single screw can safely secure each probe unit to the probe holder since the probe unit is pressed against the inner surface of the probe holder during rotation of the probe holder.

It is to be understood that even through several characteristics and advantages of the present invention have been set forth in the foregoing description, together with details of the structure and function of the invention, the disclosure is illustrative only. Accordingly, changes may be made in detail, especially in matters of shape, size and arrangement of parts within the scope of the invention.

What is claimed is:

1. An ultrasonic pipe inspection system comprising:
   an inner sleeve including at least one opening:
   an outer sleeve disposed in coaxial relation to said inner sleeve, said outer sleeve having a substantially cylindrical inner surface and cooperating with said inner sleeve to define an annular passage therebetween;
   means for rotating said inner sleeve and said outer sleeve together;
   means for providing a contact medium, said contact medium being introduced to said annular passage and injected to a test piece through said at least one opening of said inner sleeve while the test piece is passing axially through said inner sleeve; and
   means for transmitting ultrasonic waves to the test piece to detect flaws therein, said means for transmitting ultrasonic waves including at least one probe unit in radial alignment with said at least one opening of the inner sleeve;
   said at least one probe unit extending radially from the inner surface of said outer sleeve toward said at least one opening.

2. The system of claim 1, wherein said at least one probe unit comprises a probe casing, and a probe received in said probe casing, and wherein said inner surface of said outer sleeve has a recess to receive said probe casing.

3. The system of claim 2, wherein said probe casing and said recess have substantially flat bottoms.

4. The system of claim 2, wherein said means for rotating comprises an electric motor and a mount, and said mount has one end connected to said electric motor, wherein said mount has a flange at its other end, and said inner sleeve has one end connected to said flange of said mount, and wherein said inner sleeve has a flange at its other end, and said outer sleeve extends between said flange of said inner sleeve and said flange of said mount.

5. An ultrasonic pipe inspection system comprising:
   an inspection body having
   means for moving a test piece of a substantially circular section through said inspection body;

a probe holder rotatably mounted in said inspection body and having a substantially cylindrical inner wall;

a nozzle block rotatably disposed in said inspection body together with said probe holder and including an axial bore, said nozzle block having a plurality of radial nozzle openings and cooperating with said probe holder to define an annular space therebetween;

a water source for providing water, said water being supplied to said annular space and injected to the test piece while the test piece is passing through said axial bore of said nozzle block; and a plurality of probes held in place by said probe holder, said plurality of probes being adapted to transmit ultrasonic waves into the test piece through said radial nozzle openings so as to detect flaws therein;

said plurality of probes extending radially from the inner wall of said probe holder toward said plurality of corresponding nozzle openings.

6. An ultrasonic pipe inspection system comprising:

first means for defining an annular chamber, said first means including a hollow inner cylinder, and an outer cylinder connected to said inner cylinder and having an inner wall, said inner cylinder including a radial opening;

second means for feeding a couplant to said annular chamber;

third means for rotating said inner and outer cylinders together; and fourth means for transmitting ultrasonic waves to a test piece of a substantially circular section while the test piece is passing axially through said inner cylinder;

said fourth means being mounted to the inner wall of said cylinder.

7. The system of claim 6, wherein said fourth means comprises an ultrasonic sensor, and said inner wall of said outer cylinder has a recess configured to receive said ultrasonic sensor.

8. The system of claim 4, wherein said probe casing is held in place by a single set screw.

* * * * *